(12) United States Patent
Xu et al.

(10) Patent No.: US 7,416,891 B2
(45) Date of Patent: *Aug. 26, 2008

(54) REAGENT AND METHOD FOR CLASSIFYING LEUCOCYTES

(75) Inventors: Wenjuan Xu, Nanshan (CN); Mulong Liu, Nanshan (CN)

(73) Assignee: Shenzhen Mindray Bio-Medical Electronics Co., Ltd, Nanshan, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 11/516,900

(22) Filed: Sep. 7, 2006

(65) Prior Publication Data

US 2007/0269896 A1 Nov. 22, 2007

(30) Foreign Application Priority Data

May 22, 2006 (CN) .................. 2006 1 0021028

(51) Int. Cl.
*G01N 31/00* (2006.01)
*G01N 33/48* (2006.01)

(52) U.S. Cl. .............. 436/10; 436/8; 436/17; 436/18; 436/63; 436/164; 436/166; 252/408.1; 435/2

(58) Field of Classification Search ........ 436/8, 436/10, 17, 18, 63, 164, 166, 174, 175; 252/408.1; 435/2; 422/82.05, 82.09
See application file for complete search history.

(56) References Cited

U.S. PATENT DOCUMENTS

| 4,528,274 | A | * | 7/1985 | Carter et al. ............. 436/10 |
|---|---|---|---|---|
| 5,116,539 | A | * | 5/1992 | Hamaguchi et al. ........ 516/77 |
| 5,155,044 | A | * | 10/1992 | Ledis et al. ............. 436/17 |
| 5,180,677 | A | * | 1/1993 | Di Ianni et al. .......... 436/17 |
| 5,242,832 | A | * | 9/1993 | Sakata ................. 436/17 |
| 5,250,437 | A | * | 10/1993 | Toda et al. ............. 436/10 |
| 5,389,549 | A | * | 2/1995 | Hamaguchi et al. ........ 436/10 |
| 5,496,734 | A | * | 3/1996 | Sakata ................. 436/63 |
| 5,518,928 | A | * | 5/1996 | Cremins et al. .......... 436/10 |
| 5,538,893 | A | * | 7/1996 | Sakata et al. ........... 436/10 |
| 5,618,733 | A | | 4/1997 | Sakata et al. |
| 5,639,630 | A | * | 6/1997 | Malin et al. ............ 435/28 |
| 5,677,183 | A | | 10/1997 | Takarada et al. |
| 5,731,206 | A | | 3/1998 | Ledis et al. |
| 5,786,224 | A | * | 7/1998 | Li et al. ............... 436/63 |
| 5,817,518 | A | * | 10/1998 | Li et al. ............... 436/63 |
| 5,821,128 | A | * | 10/1998 | Provost ................ 436/63 |
| 5,843,608 | A | * | 12/1998 | Li et al. ............... 436/63 |
| 5,958,776 | A | * | 9/1999 | Sakata et al. ........... 436/10 |
| 6,114,130 | A | * | 9/2000 | Veriac et al. ........... 435/7.24 |
| 6,210,969 | B1 | * | 4/2001 | Li et al. ............... 436/10 |
| 6,214,625 | B1 | * | 4/2001 | Li et al. ............... 436/10 |
| 6,869,798 | B2 | * | 3/2005 | Crews et al. ............ 436/10 |
| 7,026,110 | B1 | * | 4/2006 | Veriac et al. ........... 435/2 |

FOREIGN PATENT DOCUMENTS

| CN | 1126836 A | 7/1996 |
|---|---|---|
| EP | 0695 936 A2 | 6/1995 |
| JP | 08043381 | 2/1996 |
| WO | WO 88/07187 | 3/1988 |

OTHER PUBLICATIONS

U.S. Appl. No. 11/517,031, filed Nov. 29, 2007, Xu et al.
State Intellectual Property Office Searching Report dated Jun. 13, 2006 for Chinese Patent Application No. 200610021028.4 (cited in 11/517,032).
Office Action mailed on Mar. 07, 2008 for U.S. Appl. No. 11/517,031.
Office Action mailed on Sep. 28, 2007 for U.S. Appl. No. 11/517,031.
Notice of Allowance from U.S. Appl. No. 11/517,031 dated May 21, 2008.

\* cited by examiner

*Primary Examiner*—Maureen M Wallenhorst
(74) *Attorney, Agent, or Firm*—Stoel Rives LLP; Kory D. Christensen; Matthew S. Bethards

(57) ABSTRACT

A reagent for classifying leucocytes, including: a) at least one of surfactant selected from a cationic surfactant, an amphoteric surfactant, and the combination thereof; b) an organic compound having phenyl or heterocyclic group, wherein when the surfactant is a cationic surfactant, the organic compound is an organic compound having an anionic group; when the surfactant is an amphoteric surfactant or a combination of amphotheric and cationic surfactant, the organic compound is an organic compound having an anionic or cationic group; c) a buffer for adjusting pH.

22 Claims, 4 Drawing Sheets

REAGENT AND METHOD FOR CLASSIFYING LEUCOCYTES

FIELD OF THE INVENTION

The present invention relates to a reagent and a method for classifying cells, especially to a reagent and a method for classifying leucocytes in blood.

BACKGROUND ART

It is common and important to classify and count leucocytes to diagnose various diseases using the whole blood of patients in the field of a clinical test.

Up to now, many patents in regard to devices and methods for classifying leucocytes have been reported. For example, a method for dividing leukocytes into five types using two reagents has been disclosed in China Patent Application No. 95115317.X. Said two reagents both contain nonionic surfactant and buffer, and the first reagent further contains at least one ionic surfactant and one organic compound having an anionic group, to divide leukocytes into four groups, lymphocytes, monocytes, eosinophils and basophils plus neutrophils, and the second reagent further contains at least one ionic surfactant, to divide blood cells into basophils and other cells. Thus, Leukocytes are classified into five types by the combination of the two results. The measurement method used is laser scattering measurement.

Besides, U.S. Pat. Nos. 5,677,183, 5,618,733 and 5,731, 206, and a Chinese Patent Application No. 88101677 also disclosed the method for dividing leucocytes into five types based on the signals of the scattered light from two channels.

It is found, however, that monocytes are usually classified as between the lymphocytes and neutrophils when classifying leucocytes using the conventional methods mentioned above. The clustering effect is not obvious, which results in an inaccuracy of classification.

SUMMARY OF THE INVENTION

An object of the present invention is to provide a reagent and a method for rapidly lysing erythrocytes and classifying leucocytes in one channel, increasing the clustering effect of monocytes, and improving the classification effect of monocytes, thereby improving the accuracy of classification.

To realize the above objects, the present invention adopts the following technical solutions with respect to an improved reagent for classifying leucocytes, comprising a) a surfactant capable of lysing erythrocytes and partly damaging cell membrane of leucocytes, said surfactant is at least one of the surfactants selected from a cationic surfactant, an amphoteric surfactant, and the combination thereof;

b) an organic compound having phenyl or heterocyclic group, when said surfactant is a cationic surfactant, said organic compound is an organic compound having an anionic group; when said surfactant is an amphoteric surfactant or a combination of amphotheric and cationic surfactants, said organic compound is an organic compound having an anionic or cationic group;

c) a buffer for adjusting pH.

The above reagent may further comprise at least one of alcohols which is used as a cosolvent and can accelerate the reaction.

The above reagent may also further comprise at least one of acidic organic compounds and/or pigments.

Preferably, the buffer can adjust the range of pH between 2 and 6.

The cationic surfactant is preferably at least one of the quaternary ammonium salts represented by formula I,

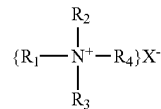

wherein, $R_1$ is $C_{6-14}$ alkyl or $C_{6-14}$ alkenyl, preferably hexyl, octyl, decyl, or dodecyl; $R_2$ and $R_3$ are independently $C_{1-4}$ alkyl or $C_{1-4}$ alkenyl, preferably methyl, ethyl, or propyl; $R_4$ is $C_{1-4}$ alkyl, $C_{1-4}$ alkenyl, or benzyl; and X is a halogen atom.

The amphoteric surfactant is preferably at least one of the surfactants represented by formula II,

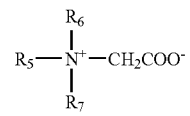

wherein, $R_5$ is a $C_{6-14}$ alkyl or $C_{6-14}$ alkenyl, preferably hexyl, octyl, decyl, or dodecyl; and $R_6$ and $R_7$ are independently $C_{1-4}$ alkyl or $C_{1-4}$ alkenyl, preferably methyl, ethyl, or propyl.

The present invention also relates to a method for classifying leukocytes using the reagent of the invention. The method comprises steps of adding said reagent to the whole blood sample for classifying leukocytes into four groups consisting of three groups corresponding to lymphocytes, monocytes and eosinophils and one group corresponding to neutrophils and basophils, and counting each group by measuring the size and the shape thereof.

The measurement of the size is performed by using laser scattering with a low angle scattered light and the measurement angle ranges from 2 to 6 degree; and the measurement of shape is performed by using laser scattering with a high angle scattered light and the measurement angle ranges from 8 to 20 degree.

The advantages of the present invention are obvious through implementing the technical solution mentioned above, which lie in that:

The reagent and method of the present invention can not only classify the leukocytes into four groups consisting of three groups corresponding to lymphocytes, monocytes and eosinophils and one group corresponding to neutrophils and basophils, but also can clearly differ monocytes from lymphocytes and neutrophils with obvious clustering effect. Moreover, various proportional monocytes can form individual scattered dot areas at stable locations and are not affected by the nucleus movement after the blood sample treated by reagents is measured by scattered light. Therefore, the resulting classification shows more accurately the real state of the blood.

DETAILED DESCRIPTION OF THE PREFERRED EMBODIMENTS

Figure 1:
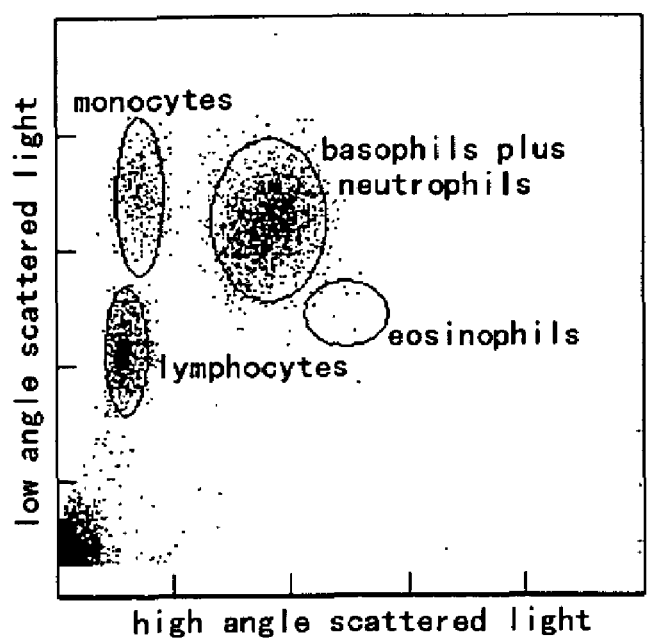
FIG. 1 is a scattergram showing dividing leukocytes into four groups and counting them using the low-angle scattered light and the high-angle scattered light after blood sample A is treated with the reagent of example 1 of the present invention.

The reagent and method of the present invention can not only divide leukocytes in the whole blood into four groups consisting of three groups corresponding to lymphocytes, monocytes and eosinophils and one group corresponding to neutrophils and basophils, but also improve the accuracy of classification for the monocytes.

When adding the reagent of the present invention into the whole blood sample, the component of the reagent lyses erythrocytes rapidly and makes various types of leucocytes vary in size and morphology, thereby classifying leukocytes into four groups consisting of three groups corresponding to lymphocytes, monocytes and eosinophils and one group corresponding to neutrophils and basophils. Then the laser scattering measurement is used, i.e., using the low angle scattered light to measure the size of the cells and the high angle scattered light to measure the morphological information of the cells, and thereby classifying and counting the leukocytes of four groups by detecting the scattered lights. The classified monocytes show obvious clustering effect and can be clearly differed from lymphocytes and neutrophils. Moreover, various proportional monocytes can form individual scattered dot areas at stable locations and are not affected by the nucleus movement after the blood sample treated by reagents is measured by scattered light. Therefore, the resulting classification shows more accurately the real state of the blood.

The main components of the reagent according to the present invention comprise:

a) a surfactant capable of lysing erythrocytes and partly damaging cell membrane of leucocytes, said surfactant is at least one of the surfactants selected from a cationic surfactant, an amphoteric surfactant, and the combination thereof;

b) an organic compound having phenyl or heterocyclic group, when said surfactant is a cationic surfactant, said organic compound is an organic compound having an anionic group; when said surfactant is an amphoteric surfactant or a combination of amphotheric and cationic surfactants, said organic compound is an organic compound having an anionic or cationic group;

(c) a buffer for adjusting pH.

The cationic surfactant is preferably at least one of quaternary ammonium salts represented by formula I,

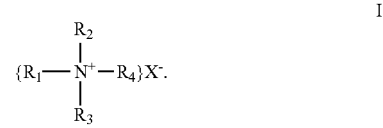

Formula I represents a cationic surfactant having totally 9-26 carbon atoms, wherein, $R_1$ is $C_{6-14}$ alkyl or $C_{6-14}$ alkenyl, preferably hexyl, octyl, decyl, dodecyl or tetradecyl, more preferably a linear alkyl comprising hexyl, octyl, decyl or dodecyl; $R_2$ and $R_3$ are independently $C_{1-4}$ alkyl or $C_{1-4}$ alkenyl, preferably methyl, ethyl, propyl, butyl or butenyl, more preferably methyl, ethyl or propyl; $R_4$ is $C_{1-4}$ alkyl, $C_{1-4}$ alkenyl, or benzyl; and X is a halogen atom.

The amphoteric surfactant is preferably at least one of the surfactants represented by formula II,

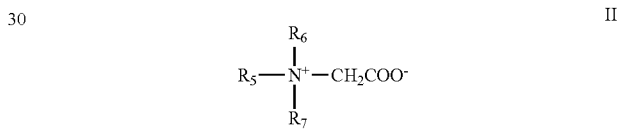

wherein, $R_5$ is $C_{6-14}$ alkyl or $C_{6-14}$ alkenyl, preferably hexyl, octyl, decyl, dodecyl or tetradecyl, more preferably a linear alkyl comprising octyl, decyl or dodecyl; $R_6$ and $R_7$ are independently $C_{1-4}$ alkyl or $C_{1-4}$ alkenyl, preferably methyl, ethyl, propyl, butyl, or butenyl, more preferably methyl, ethyl or propyl.

The surfactant is used in an amount sufficient to lyse erythrocytes and partly damage cell membranes of leucocytes. Typically, a suitable amount of the surfactant to be used in the improved reagent according to the invention is 50-6,000 mg/L, preferably 200-5,000 mg/L, more preferably 500-4,000 mg/L, though it can be suitably modified depending upon the type of surfactant used.

The reagent with suitable amount can completely separate monocytes from lymphocytes in size, and the monocytes have stable locations. Meanwhile, the monocytes can be easily differed from granulocytes in morphology, which benefits for cell counting.

Some surfactants and suitable amounts thereof according to the present invention are listed in Table 1.

TABLE 1

| Most Suitable amounts for the following surfactants | |
|---|---|
| Surfactant | Amount (mg/L) |
| Decyltrimethylammonium bromide (DTAB) | 1000-2500 |
| dodecyltrimethylammonium chloride | 1000-2000 |
| dodecyltrimethylammonium bromide | 1000-1500 |
| dodecylpyridinium chloride | 500-1500 |
| tetradecyltrimethylammonium chloride | 500-1000 |

TABLE 1-continued

Most Suitable amounts for the following surfactants

| Surfactant | Amount (mg/L) |
|---|---|
| tetradecyltrimethylammonium bromide | 500-1000 |
| Decylglutamic acid | 500-5000 |
| dodecylglutamic acid | 500-4000 |
| tetradecylglutamic acid | 500-3000 |
| Decylglycine | 500-5000 |
| dodecylglycine | 500-4000 |
| tetradecylglycine | 500-3000 |

A useful surfactant according to the present invention is capable of lysing the leucocytes to such an extent that it makes pores on cell membranes and the cytoplasm can overflow out from the leucocytes and an organic compound binding with a cationic group can enter, and the amount of the surfactant used is much less than that amount which is potent to make the cell nuclei naked. The effect of hemolysis for a surfactant is in proportion to the number of carbon atoms on the side chain thereof (i.e., $R_1$ of cationic surfactant and $R_5$ of amphoteric surfactant), the more the numbers of carbon atoms, the more the capacity of hemolysis, and further the required amount is lower.

Another main component of the reagent according to the present invention is organic compound having phenyl or heterocyclic group. When the used surfactant is a cationic surfactant, the organic compound is selected from an organic compound having an anionic group; when the surfactant used is an amphoteric surfactant or a combination of amphotheric and cationic surfactants, the organic compound is selected from an organic compound having an anionic group or a cationic group. The heterocyclic group is selected from those with 5 ring atoms or more.

An organic compound having an anionic or cationic group used in the present invention is capable of bonding with various ions in leukocytes, resulting in morphological differentiations among the various groups of leukocyte. Such organic compound contains phenyl or heterocyclic group having 5 or more ring atoms, and an anionic group (e.g., carboxyl or sulfonic group) or a cationic group (e.g., $N^+$, or $NH4^+$). A cationic organic compound may comprise pyridine, pyrrole, 2-pyridinyl thiourea, 2-naphthylamine, etc., and an anionic organic compound may comprise 1-naphthylacetic acid, naphthalene-1,4,5,8-tetracarboxylic acid, terephthalic acid, phthalic acid, chromotropic acid, naphthalene sulfonic acid and their derivatives and salts thereof. The amount of the organic compound in the reagent according to the present invention is typically 50-1000 mg/L, preferably 100-500 mg/L.

The reagent according to the present invention further comprises a buffer for adjusting pH. There are no particular limitations to the buffer. It may be a conventional buffer system, such as formic acid, phthalic acid, acetic acid, phosphoric acid, TRIS, boric acid, carbonic acid, etc. The range of pH has no essential influence on the classification of four groups, however the classification effect of monocytes can be improved by adjusting pH. In the present invention, a preferable pH of the reagent for classifying monocytes is 2-6, and the amount of buffer used in the reagent of the invention is 10-200 mM.

In addition, the reagent according to the present invention may also comprise an alcohol which is used as a cosolvent and can accelerate the reaction. There are no particular limitations to the alcohol used herein. It may be methanol, ethanol, iso-propanol or 2-phenoxyethanol, etc. The amount of an alcohol is 0.05-5% (v/v) relative to the total amount of the reagent of the present invention.

Further, to improve the separation effect of eosinophils from granulocytes, a certain amount of organic compounds or pigments can be added to the reagent of the present invention, such as acid blues, direct blue, acid greens, acid yellows, acid oranges, methyl reds, methyl orange, aniline blue or alizarin yellow, etc. The amount is 50-1000 mg/L, preferably 100-500 mg/L.

Further, a certain amount of NaCl can be added to the reagent of the present invention to adjust osmotic pressure of the solution to a suitable range.

The reagent of the present invention may be prepared as one reagent or a combination of two reagents. When using the combination of two reagents, the pHs of the two reagents can be the same or not.

The method of the present invention for classifying leukocytes comprises adding the reagent of the present invention to the whole blood sample and mixing for a period of time, detecting the size and morphological information of the various cells, thereby classifying leukocytes into four groups consisting of three groups corresponding to lymphocytes, monocytes and eosinophils, and one group corresponding to neutrophils and basophils according to the differences of the size and morphology of the cells, and meanwhile counting each group of cells.

The mixing ratio of the whole blood sample to the reagent of the invention has no particular limitation, and typically the ratio is 1:10-100. The measurement can be carried out after 30 seconds of the mixing.

The preferred method for measuring the size and morphology of cells is laser scattering measurement. The size is measured by the low angle scattered light with angle ranging from 2 to 6 degree, and the morphological information is measured by the high angle scattered light with angle ranging from 8 to 20 degree. A conventional photodiode sensor can be employed to detect the scattered light.

EXAMPLES

The following non-limiting examples illustrate the reagent and the method of the invention.

Example 1

A reagent for dividing leukocytes into four groups☐comprising:

| | |
|---|---|
| NaCl | 0.3 g |
| Ethanol | 2.0 g |
| Glycerol | 0.75 g |
| Octyltrimethylammonium bromide | 8.1 g |
| 1-Naphthylacetic acid | 0.4 g |
| Acetic acid | 1.95 g |
| Acid blue | 0.15 g |
| Water | q.s to 1 L |
| pH | 3.8 |

The resultant reagent is adjusted to have pH of 3.8 and osmotic pressure of 135 mOsm.

Adding 0.98 mL of the above resultant reagent to 30 µL of blood sample A, and after mixing for 13 seconds the leukocytes are measured by laser scattering measurement. The size information of cells is obtained by using the low angle scattered light with angle ranging from 2 to 6 degree, and the morphology information of cells is obtained by using the high angle scattered light with angle ranging from 8 to 20 degree.

FIG. 1 shows the measurement result that monocytes form individual scattered dot areas at stable locations with an obvious clustering effect. Moreover, the monocytes can be clearly differed from lymphocytes and neutrophils. Meanwhile, the leukocytes are divided into four groups, lymphocytes, monocytes, eosinophils and neutrophils plus basophils.

Example 2

A reagent for dividing leukocytes into four groups comprising:

| NaCl | 0.3 g |
|---|---|
| Ethanol | 2.0 g |
| Glycerol | 0.75 g |
| decyldimethylammonium oxide | 5.8 g |
| 1-Naphthylacetic acid | 0.4 g |
| Acetic acid | 2 g |
| Acid blue | 0.15 g |
| Water | q.s. to 1 L |
| pH | 4.2 |

The resultant reagent is adjusted to have pH of 4.2 and osmotic pressure of 125 mOsm.

Adding 0.98 mL of the above resultant reagent to 30 μL of blood sample A, and after mixing for 13 seconds the leukocytes are measured by laser scattering measurement. The size information of cells is obtained by using the low angle scattered light with angle ranging from 2 to 6 degree, and the morphology information of cells is obtained by using the high angle scattered light with angle ranging from 8 to 20 degree.

Figure 2:
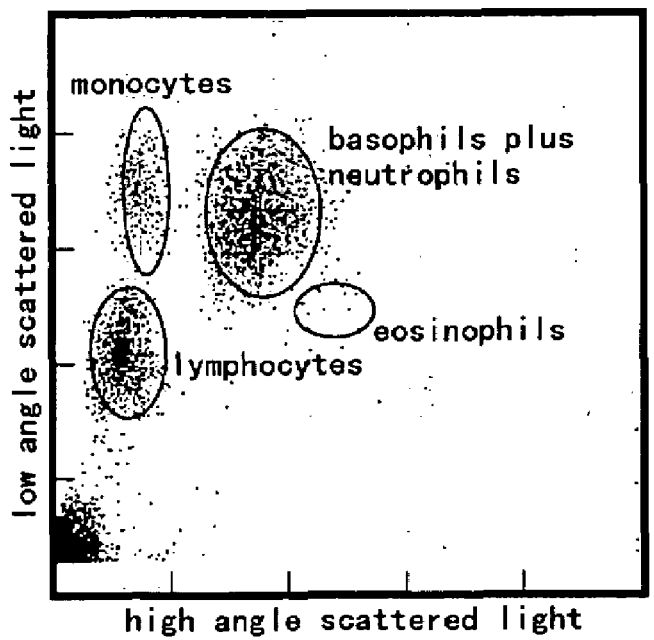
FIG. 2 is a scattergram showing dividing leukocytes into four groups and counting them using the low-angle scattered light and the high-angle scattered light after blood sample A is treated with the reagent of example 2 of the present invention.

FIG. 2 shows the measurement result that monocytes form individual scattered dot areas at stable locations with an obvious clustering effect. Moreover, the monocytes can be clearly differed from lymphocytes and neutrophils. Meanwhile, the leukocytes are divided into four groups, lymphocytes, monocytes, eosinophils and neutrophils plus basophils.

Example 3

A reagent for dividing leukocytes into four groups comprising:

| NaCl | 0.2 g |
|---|---|
| Lauryl betaine | 1.2 g |
| dodecyltrimethylammonium chloride | 2.8 g |
| 2-Phenoxyethanol | 3 g |
| Phthalic acid | 1 g |
| Acid blue | 0.4 g |
| Water | q.s. to 1 L |
| pH | 2.5 |

The resultant reagent is adjusted to have pH of 2.5 and osmotic pressure of 100 mOsm.

Adding 2 mL of the above resultant reagent to 30 μL of blood sample B, and after mixing for 15 seconds the leukocytes are measured by laser scattering measurement. The size information of cells is obtained by using the low angle scattered light with angle ranging from 2 to 6 degree, and the morphology information of cells is obtained by using the high angle scattered light with angle ranging from 8 to 20 degree.

Figure 3:
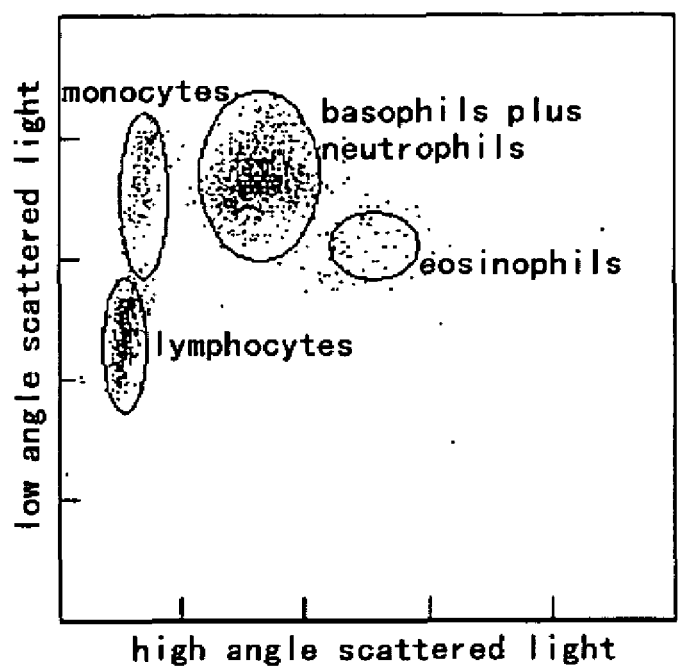
FIG. 3 is a scattergram showing dividing leukocytes into four groups and counting them using the low-angle scattered light and the high-angle scattered light after blood sample B is treated with the reagent of example 3 of the present invention.

FIG. 3 shows the measurement result that monocytes form individual scattered dot areas at stable locations with an obvious clustering effect. Moreover, the monocytes can be clearly differed from lymphocytes and neutrophils. Meanwhile, the leukocytes are divided into four groups, lymphocytes, monocytes, eosinophils and neutrophils plus basophils.

Example 4

A reagent for dividing leukocytes into four groups comprising:

| NaCl | 0.2 g |
|---|---|
| dodecylglutamic acid | 1.4 g |
| diallylammonium chloride | 5.8 g |
| 2-Phenoxyethanol | 3 g |
| Phthalic acid | 1 g |
| Acid blue | 0.4 g |
| Water | q.s. to 1 L |
| pH | 2.8 |

The resultant reagent is adjusted to have pH of 2.8 and osmotic pressure of 150 mOsm.

Adding 2 mL of the above resultant reagent to 30 μL of blood sample B, and after mixing for 15 seconds the leukocytes are measured by laser scattering measurement. The size information of cells is obtained by using the low angle scattered light with angle ranging from 2 to 6 degree, and the morphology information of cells is obtained by using the high angle scattered light with angle ranging from 8 to 20 degree.

Figure 4:
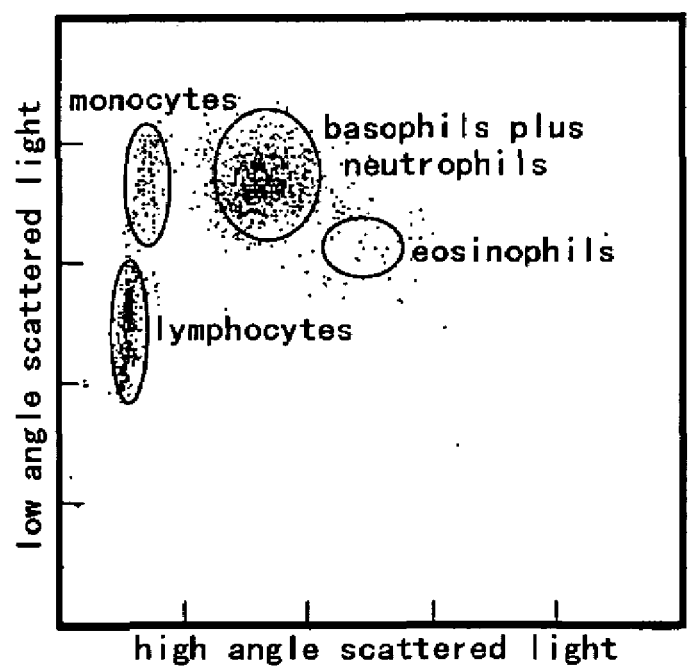
FIG. 4 is a scattergram showing dividing leukocytes into four groups and counting them using the low-angle scattered light and the high-angle scattered light after blood sample B is treated with the reagent of example 4 of the present invention.

FIG. 4 shows the measurement result that monocytes form individual scattered dot areas at stable locations with an obvious clustering effect. Moreover, the monocytes can be clearly differed from lymphocytes and neutrophils. Meanwhile, the leukocytes are divided into four groups, lymphocytes, monocytes, eosinophils and neutrophils plus basophils.

Example 5

A reagent for dividing leukocytes into four groups comprising:

| NaCl | 0.2 g |
|---|---|
| dodecylglutamic acid | 1 g |
| dimethylbenzylammonium chloride | 3.8 g |
| 2-Phenoxyethanol | 3 g |
| Phthalic acid | 1 g |
| Acid blue | 0.4 g |
| Water | q.s. to 1 L |
| pH | 3.5 |

The resultant reagent is adjusted to have pH of 3.5 and osmotic pressure of 136 mOsm.

Adding 2 mL of the above resultant reagent to 30 μL of blood sample C, and after mixing for 15 seconds the leukocytes are measured by laser scattering measurement. The size information of cells is obtained by using the low angle scattered light with angle ranging from 2 to 6 degree, and the morphology information of cells is obtained by using the high angle scattered light with angle ranging from 8 to 20 degree.

Figure 5:
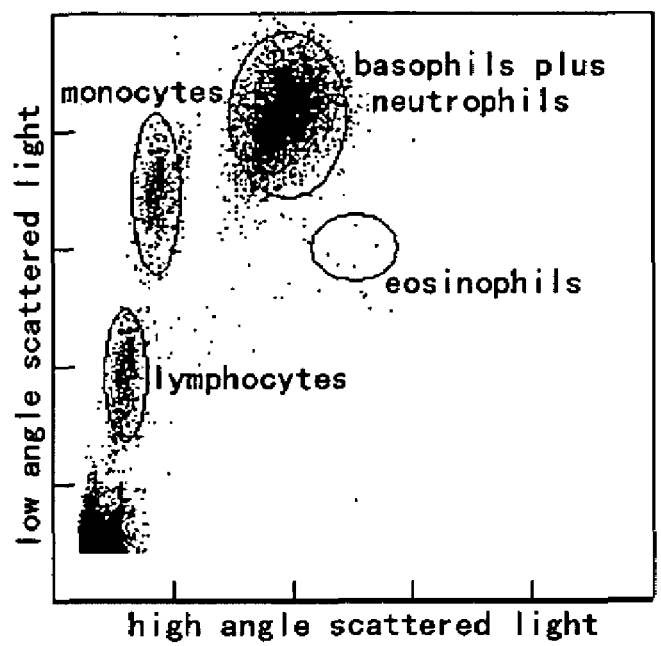
FIG. 5 is a scattergram showing dividing leukocytes into four groups and counting them using the low-angle scattered light and the high-angle scattered light after blood sample C is treated with the reagent of example 5 of the present invention.

FIG. 5 shows the measurement result that monocytes form individual scattered dot areas at stable locations with an obvious clustering effect. Moreover, the monocytes can be clearly differed from lymphocytes and neutrophils. Meanwhile, the leukocytes are divided into four groups, lymphocytes, monocytes, eosinophils and neutrophils plus basophils.

Example 6

A reagent for dividing leukocytes into four groups comprising:

| | |
|---|---|
| NaCl | 0.3 g |
| Dodecylglycine | 1 g |
| Methanol | 5 g |
| 2-Naphthylamine | 0.5 g |
| Sodium dihydrogen phosphate | 2.9 g |
| Disodium hydrogen phosphate | 2.3 g |
| Acid blue | 0.4 g |
| Water | q.s. to 1 L |
| pH | 5.8 |

The resultant reagent is adjusted to have pH of 5.8 and osmotic pressure of 200 mOsm.

Adding 1.5 mL of the above resultant reagent to 30 μL of blood sample C, and after mixing for 18 seconds the leukocytes are measured by laser scattering measurement. The size information of cells is obtained by using the low angle scattered light with angle ranging from 2 to 6 degree, and the morphology information of cells is obtained by using the high angle scattered light with angle ranging from 8 to 20 degree.

Figure 6:
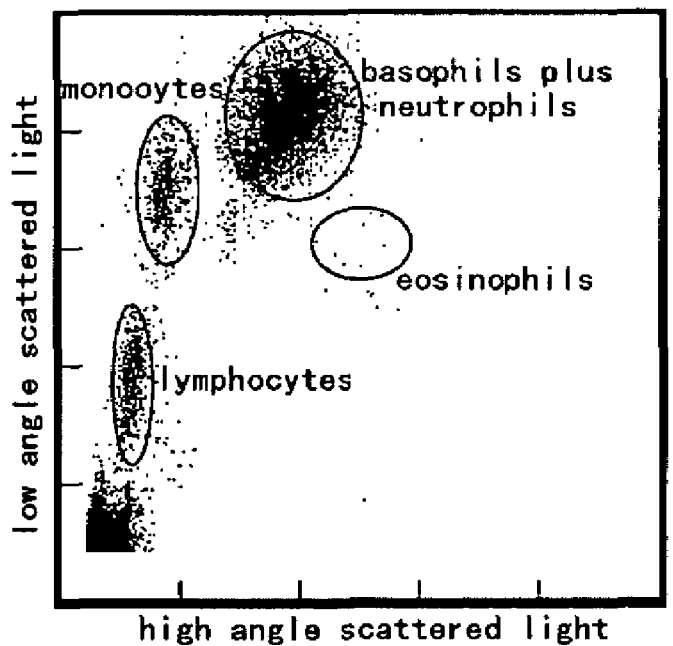
FIG. 6 is a scattergram showing dividing leukocytes into four groups and counting them using the low-angle scattered light and the high-angle scattered light after blood sample C is treated with the reagent of example 6 of the present invention.

FIG. 6 shows the measurement result that monocytes form individual scattered dot areas at stable locations with an obvious clustering effect. Moreover, the monocytes can be clearly differed from lymphocytes and neutrophils. Meanwhile, the leukocytes are divided into four groups, lymphocytes, monocytes, eosinophils and neutrophils plus basophils.

The three blood samples A, B, and C employed in above examples contain monocytes with different proportions respectively. The results show that the leukocytes can be classified into four groups by the reagent and method of the present invention, and various proportional monocytes can form individual scattered dot areas at the stable locations which is not affected by the nucleus movement. Therefore, the result of classification is more accurately to show the real state of the blood.

Contrast Test

A reagent for dividing leukocytes into four groups comprising:

| | |
|---|---|
| NaCl | 0.2 g |
| Methanol | 3 g |
| Polyoxyethylene (23) cetyl ether (Brij 35) (nonionic surfactant) | 1.4 g |
| Sodium dodecyl sulfonate SDS (anionic surfactant) | 1.2 g |
| Formic acid | 1.3 g |
| Acid blue | 0.15 g |
| Water | q.s. to 1 L |
| pH | 3.8 |

The resultant reagent is adjusted to have pH of 3.8 and osmotic pressure of 130 mOsm.

Adding 1.5 mL of the resultant reagent to 30 μL of blood samples A, B and C respectively, and after mixing for 15 seconds the leukocytes are measured by laser scattering measurement. The size information of cells is obtained by using the low angle scattered light with angle ranging from 2 to 6 degree, and the morphology information of cells is obtained by using the high angle scattered light with angle ranging from 8 to 20 degree.

Figure 7:
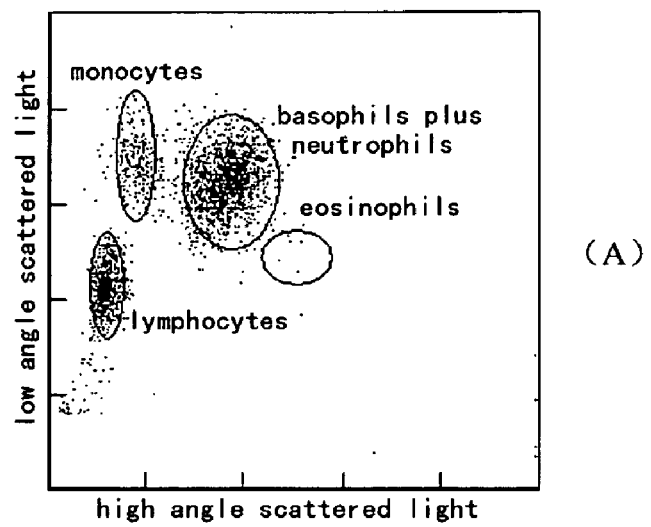
FIGS. 7 (A), (B), and (C) are scattergrams showing dividing leukocytes into four groups and counting them using the low-angle scattered light and the high-angle scattered light after blood samples A, B, and C are treated with reagents of contrast examples respectively.
Figure 7:
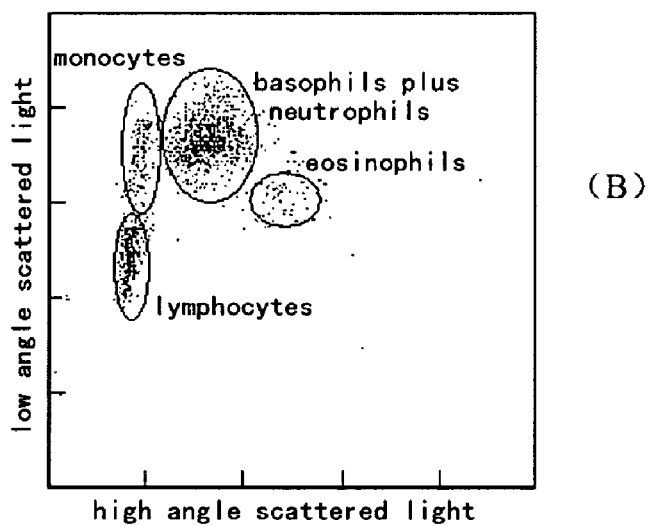
Figure 7:
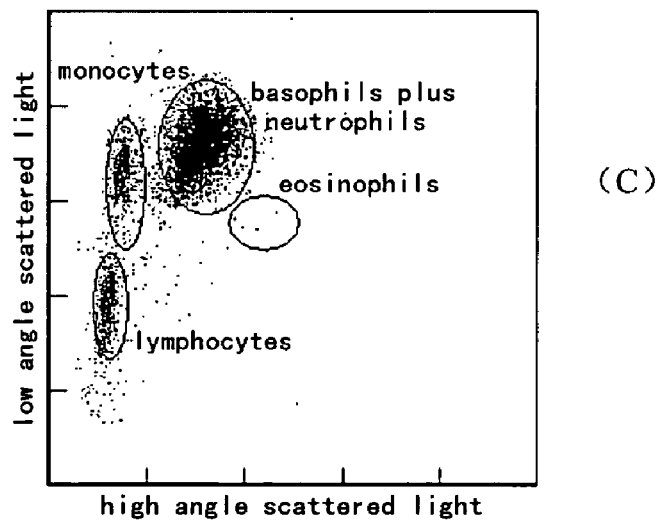

FIGS. 7 (A), (B) and (C) show the measurement result that though leukocytes are classified into four groups, lymphocytes, monocytes, eosinophils and neutrophils plus basophils, monocytes can not be clearly differed from lymphocytes and neutrophils. The clustering effect of monocytes is not shown obviously. Moreover, locations of the monocytes are not stable.

What is claimed is:

1. A reagent for classifying leucocytes, wherein said reagent comprises;
    a) a surfactant for lysing erythrocytes and partly damaging cell membrane of leukocytes, wherein the only said surfactant in the reagent is at least one of the surfactants selected from the group consisting of a cationic surfactant, an amphoteric surfactant, and the combination thereof,
    b) an organic compound having phenyl or heterocyclic group, wherein when said surfactant is a cationic surfactant, said organic compound is an organic compound having an anionic group; when said surfactant is an amphoteric surfactant or a combination of amphotheric and cationic surfactants, said organic compound is an organic compound having an anionic or cationic group; and
    c) a buffer for adjusting pH.

2. The reagent for classifying leucocytes according to claim 1, wherein said reagent further comprises an alcohol.

3. The reagent for classifying leucocytes according to claim 2, wherein the cationic surfactant is at least one of the quaternary ammonium salts represented by formula I,

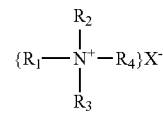

$$\{R_1 - \underset{\underset{R_3}{|}}{\overset{\overset{R_2}{|}}{N^+}} - R_4\}X^-$$  I wherein $R_1$ is $C_{6-14}$ alkyl or $C_{6-14}$ alkenyl; $R_2$ and $R_3$ are independently $C_{1-4}$ alkyl or $C_{1-4}$ alkenyl; $R_4$ is $C_{1-4}$ alkyl, $C_{1-4}$ alkenyl, or benzyl; and X is a halogen atom.

4. The reagent for classifying leucocytes according to claim 3, wherein $R_1$ is hexyl, octyl, decyl or dodecyl; $R_2$ and $R_3$ are independently methyl, ethyl or propyl.

5. The reagent for classifying leucocytes according to claim 2, wherein the amphoteric surfactant is at least one of those represented by formula II,

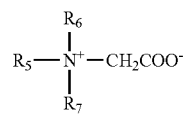

$$R_5 - \underset{\underset{R_7}{|}}{\overset{\overset{R_6}{|}}{N^+}} - CH_2COO^-$$  II wherein $R_5$ is $C_{6-14}$ alkyl or $C_{6-14}$ alkenyl; $R_6$ and $R_7$ are independently $C_{1-4}$ alkyl or $C_{1-4}$ alkenyl.

6. The reagent for classifying leucocytes according to claim 5, wherein $R_5$ is hexyl, octyl, decyl or dodecyl; $R_6$ and $R_7$ are independently methyl, ethyl or propyl.

7. The reagent for classifying leucocytes according to claim 2, wherein said reagent further comprises at least one of acidic organic compounds and/or pigments.

8. The reagent for classifying leucocytes according to claim 7, wherein the cationic surfactant is at least one of the quaternary ammonium salts represented by formula I,

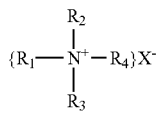

wherein $R_1$ is $C_{6-14}$ alkyl or $C_{6-14}$ alkenyl; $R_2$ and $R_3$ are independently $C_{1-4}$ alkyl or $C_{1-4}$ alkenyl; $R_4$ is $C_{1-4}$ alkyl, $C_{1-4}$ alkenyl, or benzyl; and X is a halogen atom.

9. The reagent for classifying leucocytes according to claim 8, wherein $R_1$ is hexyl, octyl, decyl or dodecyl; $R_2$ and $R_3$ are independently methyl, ethyl or propyl.

10. The reagent for classifying leucocytes according to claim 7, wherein the amphoteric surfactant is at least one of those represented by formula II,

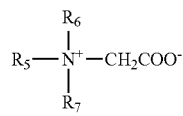

wherein $R_5$ is $C_{6-14}$ alkyl or $C_{6-14}$ alkenyl; $R_6$ and $R_7$ are independently $C_{1-4}$ alkyl or $C_{1-4}$ alkenyl.

11. The reagent for classifying leucocytes according to claim 10, wherein $R_5$ is hexyl, octyl, decyl or dodecyl; $R_6$ and $R_7$ are independently methyl, ethyl or propyl.

12. The reagent for classifying leucocytes according to claim 1, wherein said buffer is a buffer for adjusting the pH of the reagent within the range of from 2 to 6.

13. The reagent for classifying leucocytes according to claim 12, wherein the cationic surfactant is at least one of the quaternary ammonium salts represented by formula I,

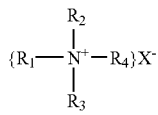

wherein $R_1$ is $C_{6-14}$ alkyl or $C_{6-14}$ alkenyl; $R_2$ and $R_3$ are independently $C_{1-4}$ alkyl or $C_{1-4}$ alkenyl; $R_4$ is $C_{1-4}$ alkyl, $C_{1-4}$ alkenyl, or benzyl; and X is a halogen atom.

14. The reagent for classifying leucocytes according to claim 13, wherein $R_1$ is hexyl, octyl, decyl or dodecyl; $R_2$ and $R_3$ are independently methyl, ethyl or propyl.

15. The reagent for classifying leucocytes according to claim 12, wherein the amphoteric surfactant is at least one of those represented by formula II,

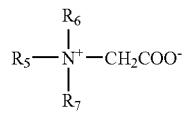

wherein $R_5$ is $C_{6-14}$ alkyl or $C_{6-14}$ alkenyl; $R_6$ and $R_7$ are independently $C_{1-4}$ alkyl or $C_{1-4}$ alkenyl.

16. The reagent for classifying leucocytes according to claim 15, wherein $R_5$ is hexyl, octyl, decyl or dodecyl; $R_6$ and $R_7$ are independently methyl, ethyl or propyl.

17. The reagent for classifying leucocytes according to claim 1, wherein the cationic surfactant is at least one of the quaternary ammonium salts represented by formula I,

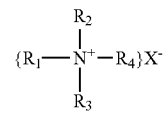

wherein $R_1$ is $C_{6-14}$ alkyl or $C_{6-14}$ alkenyl; $R_2$ and $R_3$ are independently $C_{1-4}$ alkyl or $C_{1-4}$ alkenyl; $R_4$ is $C_{1-4}$ alkyl, $C_{1-4}$ alkenyl, or benzyl; and X is a halogen atom.

18. The reagent for classifying leucocytes according to claim 17, wherein $R_1$ is hexyl, octyl, decyl or dodecyl; $R_2$ and $R_3$ are independently methyl, ethyl or propyl.

19. The reagent for classifying leucocytes according to claim 1, wherein the amphoteric surfactant is at least one of those represented by formula II,

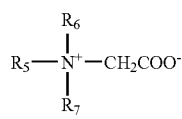

wherein $R_5$ is $C_{6-14}$ alkyl or $C_{6-14}$ alkenyl; $R_6$ and $R_7$ are independently $C_{1-4}$ alkyl or $C_{1-4}$ alkenyl.

20. The reagent for classifying leucocytes according to claim 19, wherein $R_5$ is hexyl, octyl, decyl or dodecyl; $R_6$ and $R_7$ are independently methyl, ethyl or propyl.

21. A method for classifying leukocytes using the reagent according to claim 1, comprising steps of adding said reagent to a whole blood sample for classifying leukocytes into four groups consisting of three groups corresponding to lymphocytes, monocytes and eosinophils and one group corresponding to neutrophils and basophils, and counting each group by measuring the size and the shape thereof, wherein the measurement of the size of the cells is performed by using laser scattering with a low angle scattered light at a measurement angle ranging from 2 to 6 degrees and the measurement of the shape of the cells is performed by using laser scattering with a high angle scattered light at a measurement angle ranging from 8 to 20 degrees; wherein a scattergram produced by counting each group using low angle scattered light and high angle scattered light provides the monocyte group spaced apart from the remaining leukocyte groups.

22. A reagent for classifying leucocytes, said reagent consisting essentially of:
   a) a surfactant for lysing erythrocytes and partly damaging cell membrane of leucocytes, said surfactant is at least one of the surfactants selected from the group consisting of a cationic surfactant, an amphoteric surfactant, and the combination thereof,
   b) an organic compound having phenyl or heterocyclic group, wherein when said surfactant is a cationic surfactant, said organic compound is an organic compound having an anionic group; when said surfactant is an amphoteric surfactant or a combination of amphoteric and cationic surfactants, said organic compound is an organic compound having an anionic or cationic group;
   c) a buffer for adjusting pH; and
   d) optionally, an alcohol, an acidic organic compound and/or pigments.

* * * * *